United States Patent [19]

Winchell et al.

[11] Patent Number: 5,380,515

[45] Date of Patent: Jan. 10, 1995

[54] MRI IMAGE ENHANCEMENT OF BONE AND RELATED TISSUE USING COMPLEXES OF PARAMAGNETIC CATIONS AND POLYPHOSPHONATED LIGANDS

[75] Inventors: Harry S. Winchell, Lafayette, Calif.; Joseph Y. Klein, Haifa, Israel; Elliot D. Simhon, Haifa, Israel; Rosa L. Cyjon, Haifa, Israel; Ofer Klein, Haifa, Israel; Haim Zaklad, Haifa, Israel

[73] Assignee: Concat, Ltd., Lafayette, Calif.

[21] Appl. No.: 96,141

[22] Filed: Jul. 22, 1993

Related U.S. Application Data

[60] Division of Ser. No. 757,880, Sep. 11, 1991, Pat. No. 5,236,695, which is a continuation-in-part of Ser. No. 441,144, Nov. 27, 1989, abandoned.

[51] Int. Cl.$^6$ .............................. A61B 5/055
[52] U.S. Cl. ............................ 424/9; 436/173; 128/653.4; 534/15; 540/465; 540/474; 514/184; 514/836
[58] Field of Search ............... 424/9; 436/173; 128/653.4, 654; 534/15; 540/465, 474; 514/184, 836

[56] References Cited

U.S. PATENT DOCUMENTS 4,647,447 3/1987 Gries et al. .................... 424/9

FOREIGN PATENT DOCUMENTS

WO89/01476 2/1989 WIPO .

OTHER PUBLICATIONS

Kabachnik, M. I., *Chem. Abs.* 101(21):192203s. From: *Otkrytiya Izobret. Prom. Obraztsy, Tovarnye Znaki*, 23:84–85 (1984).

Primary Examiner—Gary E. Hollinden
Attorney, Agent, or Firm—Townsend and Townsend Khourie and Crew

[57] ABSTRACT

Polyphosphonate ligands containing three or more phosphonate groups, combined with paramagnetic metal cations and administered in the form of pharmacologically acceptable salts, are useful as MRI contrast enhancement agents, which tend to localize in bone tissue without being conjugated to bone-specific biomolecules. Triazacyclononanes and tetraazacyclododecanes, with dihydroxyphosphorylmethyl or dihydroxyphosphorylethyl groups, optionally substituted at the methyl or ethyl bridges with alkyl, aryl, hydroxyl or amino groups, are particularly preferred.

46 Claims, No Drawings

MRI IMAGE ENHANCEMENT OF BONE AND RELATED TISSUE USING COMPLEXES OF PARAMAGNETIC CATIONS AND POLYPHOSPHONATED LIGANDS

CROSS REFERENCE TO RELATED APPLICATION

This is a Division of application Ser. No. 07/757,880 filed Sep. 11, 1991, now U.S. Pat. No. 2,236,695, which is a continuation-in-part of application Ser. No. 07/441,144, filed Nov. 27, 1989, abandoned.

This invention lies in the field of magnetic resonance imaging, and is relevant to the art of contrast enhancement agents used in connection with magnetic resonance imaging in medical diagnostics.

BACKGROUND OF THE INVENTION

The availability of magnetic resonance imaging (MRI) devices has led to the use of MRI in medical examinations for the detection and diagnosis of disease states and other internal abnormalities. The continued use and development of MRI has stimulated interest in the development of pharmaceutical agents capable of altering MRI images in diagnostically useful ways. Pharmaceutical agents (MRI pharmaceuticals) which are currently favored by researchers in the field are suitably complexed paramagnetic metal cations. The use of pharmaceuticals in MRI imaging offers major opportunities for improving the value of the diagnostic information which can be obtained.

Radiopharmaceuticals, which are used in radioisotopic imaging in a manner analogous to MRI pharmaceuticals, are a well developed field. The knowledge existing in this field thus provides a staring point for the development of MRI pharmaceuticals. MRI pharmaceuticals must meet certain characteristics, however, which are either not required or are considerably less critical in the case of radiopharmaceuticals. MRI pharmaceuticals must be used in greater quantities than radiopharmaceuticals. As a result, they must not only produce detectable changes in proton relaxation rates but they must also be (a) substantially less toxic, thereby permitting the use of greater amounts, (b) more water soluble to permit the administration of a higher dosage in physiologically acceptable volumes of solution, and (c) more stable in vivo than their radiopharmaceutical counterparts. In vivo stability is important in preventing the release of free paramagnetic metals and free ligand in the body of the patient, and is likewise more critical due to the higher quantities used. For the same reasons, MRI pharmaceuticals which exhibit whole body clearance within relatively short time periods are particularly desirable.

Since radiopharmaceuticals are administered in very small dosages, there has been little need to minimize the toxicity of these agents while maximizing water solubility, in vivo stability and whole body clearance. It is not surprising therefore that few of the ligands developed for use as components in radiopharmaceutical preparations are suitable for use in preparation of MRI pharmaceuticals. A notable exception is the well known ligand diethylene triamine pentaacetic acid (DTPA), which has proved useful in forming complexes with both radiocations, pharmacologically suitable salts of which provided useful radiopharmaceuticals, and paramagnetic cations such as gadolinium, whose pharmacologically suitable salts have proved useful as MRI pharmaceuticals.

Certain groups of radiopharmaceuticals tend to localize in bone tissue, and are thus of use in providing diagnostic information concerning bone disorders. The properties of these agents which lead to their localization in bone also allow for them to localize in soft tissues beating recognitions features in common with bone. Thus, many radiopharmaceuticals which localize in bone are known, or believed, to localize in soft tissues which are found to have gross, microscopic or chemical evidence for deposition of calcium salts (e.g., metastatic calcification), such as might occur in association with tissue injury. Thus, radiopharmaceuticals have shown localization in rhabdomyolysis of various origins, in collagen disorders and in other injured tissues. Localization of such agents in areas of myocardial infarction is an example of one application which has proven diagnostically useful. Radiopharmaceuticals which localize in bone have also been shown to localize in normal and malignant breast tissue, in pleural effusions, in infarctions of the spleen and bowel, inflammatory bowel disease, radiation injury, metastatic calcification, and in a variety of malignant tumors, etc. Regardless of the mechanism of such localization we herein refer to the soft tissues which concentrate agents which localize in bone as "bearing recognition features in common with bone." Exclusive of their localization in bone and tissues bearing recognition features in common with bone, these agents generally are distributed in the extracellular fluid spaces of the body and therefore can be used to provide information concerning the content and kinetics of the extracellular fluid of normal and abnormal tissues. One example of the clinical utility of this behavior is the detection of disruption of the blood brain barrier wherein extracellularly distributed agents abnormally localize in the region of such disruption. Most of the presently known agents which localize in bone are excreted from the body by the kidneys and therefore can be used to evaluate the renal excretory system. It is possible that such agents could be made more lipophilic such that they would be excreted by the liver, and therefore could be used to evaluate the hepatobiliary excretory system.

Agents which localize in bone and which provide MRI contrast enhancement could be used to perform similar diagnostic procedures employing radiopharmaceuticals which localize in bone. Given the substantially greater spatial and temporal resolution of MRI techniques, as compared to nuclear medical techniques, it is anticipated that useful diagnostic information could be obtained in abnormalities which were not detected using nuclear medical techniques, as for example in detection of small areas of tissue damage and/or in small regions of deposition of calcium salts. Moreover, fixation of MRI contrast enhancement agents in such tissue would be expected to increase the relaxivity of the agent by decreasing the molecular rotation rate thereby increasing signal intensity. However, known radiopharmaceutical agents which localize in bone are retained in the region of their deposition for very prolonged periods of time making them unsuitable for use as MRI contrast agents. Moreover, these "bone seeking" pharmaceuticals which contain phosphonate groups are also known to be relatively strong chelators of calcium ions and their administration at the dose and dose rate levels associated with the use of MRI contrast agents can be associated with induction of acute hypocalcemia and attendant cardiac arrest. At present, MRI contrast enhancement agents are not available which, while showing diagnostically useful localization in bone, also show near quantitative whole body clearance within acceptable time periods and which have low toxicity comparable to existing MRI contrast enhancement agents.

Most known MRI pharmaceuticals when administered in vivo do not by themselves localize in specific tissues, but instead generally distribute in extracellular fluid space in a nonspecific manner. One means of achieving localization of these inherently nonspecific pharmaceuticals in selected tissues is by conjugation with biomolecules which localize in the region of interest. Another means is by incorporating the complexes into bodies which localize in the region of interest. Hormones, albumins, liposomes, and antibodies have been mentioned in such attachments or incorporation. See Gries, H., et al., U.S. Pat. No. 4,647,447, Mar. 3, 1987.

SUMMARY OF THE INVENTION

It has now been discovered that preferential MRI image enhancement in bone tissue and other tissue bearing biospecific recognition features in common with bone is achieved by the use of ligands which bear this recognition specificity, combined with paramagnetic metal cations and administered in the form of pharmacologically acceptable salts. These complexes are fully suitable for use as MRI contrast enhancement agents, and tend to localize in bone tissue without either being conjugated to bone-specific biomolecules or being incorporated into bone localizing bodies. These agents show near quantitative whole body clearance and low in vivo toxicity, and possess all of the requirements of MRI contrast enhancement agents. Ligands containing phosphonate groups are preferred, and further preferred are ligands containing three or more phosphonate groups, preferably bonded through alkyl bridges to nitrogen atoms. Cyclic groups are still further preferred, notably polyazacycloalkanes. Particularly preferred ligands are triazacyclononanes and tetraazacyclododecanes, with dihydroxyphosphorylmethyl or dihydroxyphosphorylethyl groups attached to the nitrogen atoms, these groups optionally substituted at the methyl or ethyl bridges with alkyl, aryl, hydroxyl or amino groups. Moreover, paramagnetic complexes of phosphonate ligands derived from triazacyclanes represent a heretofore unrecognized group of contrast agents fully suitable for use as general MRI contrast enhancement agents.

DETAILED DESCRIPTION OF THE INVENTION AND PREFERRED EMBODIMENTS

Among the ligands used in the practice of the present invention are the embodiments represented by the following formulas:

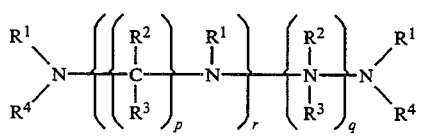

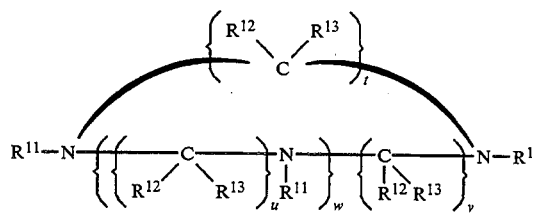

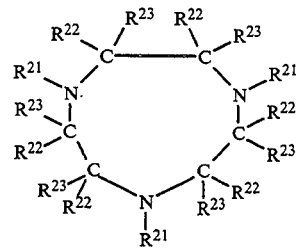

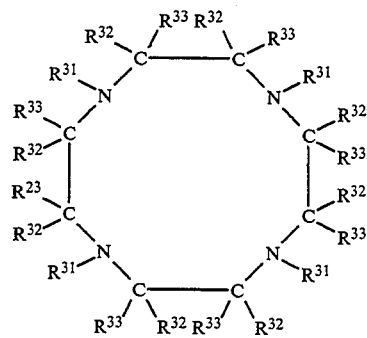

The $R^1$, $R^4$, $R^{11}$, $R^{21}$ and $R^{31}$ groups in these formulas are phosphonate groups which may be the same of different on any particular species, and are generally represented by

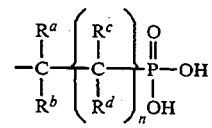

in which:

$R^a$, $R^b$ and $R^c$ are independently H, or alkyl or aryl group which do not interfere with complexation;

$R^d$ is H, OH, $NH_2$, or alkyl or aryl groups which do not interfere with complexation; and n is zero or 1.

In this definition of $R^1$, $R^4$, $R^{11}$, $R^{21}$, and $R^{31}$, certain classes of compounds are preferred. For those species in which n is 1, one preferred class is that in which $R^a$, $R^b$ and $R^c$ are each H; and $R^d$ is H, OH, $NH_2$, $C_1$–$C_8$ alkyl, phenyl or benzyl. Another preferred class is that in which $R^a$, $R^b$ and $R^c$ are each H; and $R^d$ is H, OH, $NH_2$, $C_1$–$C_4$ alkyl or benzyl. For those species in which n is zero, a preferred class is that in which $R^a$ and $R^b$ are independently H, $C_1$–$C_4$ alkyl or benzyl, while another preferred class is that in which $R^a$ and $R^b$ are independently H, $C_1$–$C_4$ alkyl or benzyl, and still another preferred class is that in which $R^a$ is H and $R^b$ is H, $C_1$–$C_4$ alkyl or benzyl.

The two $R^4$ groups in Formula I may alternatively be joined together as a single divalent group bridging the two end nitrogen atoms and having the formula

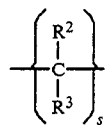

in which $R^2$ and $R^3$ are as defined below, and s is at least 2, preferably 2 or 3.

The $R^2$, $R^{12}$, $R^{22}$ and $R^{32}$ groups in these formulas may also be the same or different on any single species, and are each independently H or alkyl, aryl or mixed alkyl aryl group (such as alkyl aryl ethers) which do not interfere with complexation.

Similarly, the $R^3$, $R^{13}$, $R^{23}$ and $R^{33}$ groups in these formulas may also be the same or different on any single species, and are each independently H or alkyl, aryl or mixed alkyl aryl groups (such as alkyl aryl ethers) which do not interfere with complexation.

In Formula I, the subscripts p and q may be the same or different, and are each either 2 or 3. The subscript r is 0 to 3 inclusive, preferably 0 to 2 inclusive, and most preferably 0 or 1.

In Formula II, t, u and v may be the same or different, and are each either 2 or 3. The value of w is at least 1, more preferably 1 to 4 inclusive, still more preferably 1 to 3 inclusive, and most preferably either 1 or 2.

In preferred embodiments, all $R^1$, $R^{11}$, $R^{21}$ or $R^{31}$ groups on any single species are the same. In further preferred embodiments, all $R^2$, $R^{12}$, $R^{22}$ or $R^{32}$ groups on any single species are the same, and all $R^3$, $R^{13}$, $R^{23}$ or $R^{33}$ groups on any single species are the same. In still further preferred embodiments, all $R^2$, $R^{12}$, $R^{22}$ or $R^{32}$ groups on any single species are H, and all $R^3$, $R^{13}$, $R^{23}$ or $R^{33}$ groups on any single species are the same and are H or alkyl or aryl groups which do not interfere with complexation. In still further preferred embodiments, all $R^2$, $R^{12}$, $R^{22}$ or $R^{32}$ groups as well as all $R^3$, $R^{13}$, $R^{23}$ or $R^{33}$ groups on any single species are H.

The complexation referred to in the descriptions of the alkyl and aryl groups is the complexation of the ligand with a paramagnetic metal cation to form a chelate. Alkyl and aryl groups which do not interfere with such complexation extend to a wide range in terms of size and configuration. Preferred alkyl groups are those having 1 to 8 carbon atoms, with 1 to 4 carbon atom alkyls more preferred, and methyl and ethyl the most preferred. Both straight-chain and branched-chain alkyls are included. Preferred aryl groups are benzyl and phenyl, particularly benzyl.

Paramagnetic metals of a wide range are suitable for complexation with these ligands in the formation of the contrast enhancement agents of the present invention. These metals tend to focus in elements having atomic numbers of 22-29 (inclusive), 42, 44 and 58-70 (inclusive), and have oxidations states of 2 or 3. Of these, the ones having and atomic number of 22-29 (inclusive) and 58-70 (inclusive) are preferred, and those having atomic numbers of 24-29 (inclusive) and 64-68 (inclusive) are more preferred. Examples of such metals are chromium (III), manganese (II), iron (II), iron (III), cobalt (II), nickel (II), copper (II), praseodymium (III), neodymium (III), samarium (III), gadolinium (III), terbium (III), dysprosium (III), holmlure (III), erbium (III) and ytterbium (III). Chromium (III), manganese (II), iron (III) and gadolinium (III) are particularly preferred, with iron (III) the most preferred.

Physiologically or pharmacologically compatible salts of the chelates are formed by neutralizing acidic moieties on the chelate with physiologically or pharmacologically compatible cations from corresponding inorganic and organic bases and amino acids. Examples include alkali and alkaline earth metal cations, notably sodium. Further examples are primary, secondary and tertiary amines, notably, ethanolamine, diethanolamine, morpholine, glucamine, N,N-dimethylglucamine, and N-methylglucamine (commonly referred to as "meglumine"). Examples of amino acid cations are lysines, arginines and ornithines. As bases, these cations may be used in the form of oxides, hydroxides, carbonates, bicarbonates or any other base forms which will release the cations. Of the many embodiments of the present invention, one preferred class consists of the physiologically compatible salts which contain three equivalents of a physiologically compatible cation combined with the trianionic complex of Fe(III) and N,N',N''-tris(-dihydroxyphosphorylmethyl)-1,4,7-triazacyclononane at a pH of 6.8 to 7.4. (The term "trianionic" in this context denotes an anion having a charge of −3.)

The compounds of the present invention are capable of preparation by known procedures, some of which are described herein. The phosphonic acid, referred to herein as the "ligand," is first formed, followed by the formation of the chelate complex and then the physiologically compatible salt.

According to a typical procedure, compounds with a methylene bridge between the N and P atoms (i.e., those in which n in the above formulae is zero) are prepared by first treating the hydrobromide salt of the unsubstituted starting material (for example, 1,4,7-triazacyclononane or 1,4,7,10-tetraazacyclododecane) with formaldehyde and diethyl phosphite in aqueous solution to form the perethyl phosphonate ester (i.e., all acid groups esterified with an ethyl group). The ester subsequently can be hydrolyzed to the phosphonic acid ligand. Alkyl or aryl substitutions are introduced on the methylene carbon by treatment of the perethyl ester with a strong base such as butyllithium at −78° C. and an alkyl or aryl halide.

Likewise, the preparation of compounds with an ethylene bridge between the N and P atoms (n equaling 1) from the same unsubstituted starting materials is begun by treating the starting materials with diethyl 2-bromoethylphosphonate in the presence of excess $K_2CO_3$. This will form the phosphonic acid perethyl esters, which are then hydrolyzed in the same manner as the methylene bridge compounds.

Ethylene bridge compounds with a hydroxy substitution at the carbon adjacent to the P atom (i.e., as $R^d$) are prepared by using diethyl epoxyethylphosphonate in place of the diethyl 2-bromoethylphosphonate, and base is not used in the reaction. Those skilled in the art will recognize that similar compounds containing an amino substitution in the position of the hydroxy substitution can be prepared similarly using diethyl ethyleniminophosphonate.

It was discovered that the procedure for combining the ligand with a paramagnetic metal cation to form the chelate complex is critical when seeking to obtain a stable, chromatographically distinct species. In particular, for most of the complexes studied it was discovered that a stable distinct species was obtained by heating a solution of the ligand and a water soluble compound of the metal cation to a temperature of at least about 50° C., preferably at least about 80° C., and more preferably to reflux (100° C. in an aqueous system), at a pH in excess of 7.0. In preferred embodiments, separation and purification are incorporated into the process of elevation of the pH and heating. Thus, after initially adding the acid form of the ligand and the halide form of the paramagnetic cation and heating, the pH is slowly elevated by slow addition of base in an amount of equivalents equal to the charge of the metal cation. Thus, when the metal cation is Mn(II), two equivalents of base are added, and when the cation is Fe(III), three equivalents are added. The neutral form of the complex can then usually be crystallized as a solid from the solvent. While heating, the crystallized solid can be added to water and sufficient base to neutralize all remaining labile protonated sites of the complex. Following formation of the chromatographically distinct complex, the neutral form of the complex can then typically be recrystallized following reacidification. The optimum temperature and base addition rate will vary from one metal ion to the next, and is readily determined by routine experimentation. In certain cases, (e.g., the Fe(III) complex of N,N',N''-tris(dihydroxyphosphorylethyl)-1,4,7-triazacyclononane where the complex forms multiple species on acidification), crystallization of the neutral complex from acid medium was not performed, and the desired salt was obtained directly from solution.

Use of the procedure described typically results in species which are stable against degradation into multiple, chromatographically distinct species over time, and upon exposure to elevated temperature. The term "chromatographically distinct" is used herein to denote species which do not indicate separation into components when subjected to suitable chromatography.

Any water soluble form of the metal may be used. Notable examples are halide salts. Chlorides are particularly preferred. Sparingly water soluble oxides or salts may also be used. When oxides are used, addition of base is not needed to form the neutral form of the complex.

Physiological salts are prepared from the neutral forms of the complexes by conventional procedures. In a typical procedure, the desired salt of the complex is formed from the neutral form of the complex by addition of the required equivalent of the desired base. Heating until the pH stabilizes may be required. A solid form of the salt of the complex can be obtained by conventional procedures, such as, for example, lyophilization, and the solid can be reconstituted with pharmacologically suitable aqueous solutions prior to administration to patients. The number of physiological cations present in the final product is equal to the equivalents added during the step of base addition, and is readily confirmed by independent means such as elemental analysis or potentiometric titrations.

Administration of the MRI contrast agents of the present invention to a patient or subject on whom magnetic resonance imaging is to be performed is achieved by conventional procedures known in this art and disclosed in the literature. Aqueous solutions of the agents are most conveniently used. The concentrations of the agents in these solutions and the amounts administered may vary widely, the optimum in each case varying with the strength of the magnetic moment of the paramagnetic metal in the agent, the contrast enhancement strength of the chelate as a whole, the method of administration, the degree of contrast enhancement desired or needed, and the age, weight and condition of the patient or subject to whom administration is made. In most cases, best results are obtained with solutions at concentrations of about 0.05 to about 2.0 moles of the paramagnetic complex per liter, preferably about 0.1 to about 1.0 mole per liter. Likewise, best results in most cases are usually obtained with dosages ranging from about 0.01 to about 1.0 millimole of agent per kilogram of whole body weight (mM/kg), preferably from about 0.05 to about 0.5 mM/kg. Administration may be achieved by any parenteral route and method, most notably by intravenous administration. The rate of administration may likewise vary, best results generally being obtained at rates ranging from about 0.1 mM/min/kg to about 1.0 mM/sec/kg.

The following examples are offered for purposes of illustration, and are intended neither to define nor limit the invention in any manner.

EXAMPLE 1

SYNTHESES OF DIHYDROXYPHOSPHORYLMETHYL SPECIES

This example illustrates the preparation of various dihydroxyphosphorylmethyl compounds and complexes within the scope of the invention. Species based on both 1,4,7-triazacyclononane and 1,4,7,10-tetraazacyclododecane are illustrated in parallel fashion starting from the hydrobromide salts of 1,4,7-triazacyclononane and 1,4,7,10-tetraazacyclododecane, respectively.

A. Synthesis of Perethyl Esters of Nitrogen-Substituted Methylene Phosphonates 1,4,7-Triazacyclononane and 1,4,7,10-Tetraazacyclododecane The trihydrobromide salt of 1,4,7-triazacyclononane and the hydrobromide salt of 1,4,7,10-tetraazacyclododecane were combined with 3.5 equivalents, and 28 equivalents, respectively, of aqueous 37% formaldehyde solution. The mixtures were stirred for 15–30 minutes at room temperature, after which time 3.5 equivalents and 14 equivalents, respectively, of diethyl phosphite were added to each solution, and the reaction mixtures were stirred at room temperature for an additional 2–5 hours. Water was then added and the aqueous layers extracted five times with ethyl acetate. To the remaining water fractions, NaHCO$_3$ was added until the solutions were of pH approximately 7.5. The solutions were then continuously extracted with ether for 2–2.5 days. The products were obtained as oils upon evaporation of the ether and as needed were purified by chromatography, and were identified as the perethyl esters of 1,4,7-triazacyclononane and 1,4,7,10-tetraazacyclododecane, respectively, by NMR.

Those skilled in the art will recognize that this procedure can also be employed to synthesize compounds derived from substituted forms of 1,4,7-triazacyclononane and 1,4,7,10-tetraazacyclododecane where such substitutions are on the ring carbons and consist of substituted or unsubstituted alkyl or aryl groups as listed above, retaining the substitutions in the corresponding positions on the product compounds. Those skilled in the art will further recognize that this procedure can be employed in an analogous manner to synthesize other substituted and unsubstituted cyclical and linear polyamines.

B. Synthesis of Perethyl Esters of Nitrogen-Substituted Methylene Phosphonates Substituted with Benzyl Groups at the Methylene Carbon In this procedure, one of the perethyl esters prepared in part A above is converted to an analog which contains a benzyl group attached to the methylene carbon.

The perethyl ester of 1,4,7-triazaeyelononane prepared in part A above, dissolved in dry tetrahydrofuran, was combined with an excess of butyllithium at −78° C., and the reaction mixture was stirred for 30 minutes at that temperature. An amount of benzyl bromide equal to the number of equivalents of butyllithium employed was then added with stirring. The mixture was then allowed to slowly warm to room temperature. After continued stirring at room temperature for an additional 30 minutes, cold water was added and the aqueous layer was extracted with diethyl ether. The ether was evaporated and the residue chromatographed on silica gel G60 70–230 mesh to obtain the perethyl ester of N,N',N''-tris(dihydroxyphosphorylbenzylmethyl)-1,4,7-triazacyclononane, whose identity was established by proton NMR.

Those skilled in the art will recognize that this procedure can be used to place other substituted or unsubstituted alkyl or aryl halides on the methylene carbon as well, using the appropriate alkyl or aryl halide.

C. Hydrolysis of the Perethyl Esters to the Phosphonic Acids

In this procedure, both perethyl esters of part A above were converted to the corresponding phosphonic acids.

The perethyl esters were separately dissolved in concentrated hydrochloric acid and heated at 80° C. for six to eight hours. The resulting solutions were evaporated to dryness, and the pure acid forms were obtained following crystallization from water or water/ethanol. Their identity as the acids was confirmed by proton NMR and elemental analysis.

To further confirm the identity of the products, independent syntheses were performed employing the method described by Polykarpov, Yu M., et al. "N, N',N''-Tris(phosphonomethyl)-1,4,7-triazacyclononane—a specific complexing agent for magnesium ion," Izv. Akad. Nauk SSSR. Ser. Khim., 1982, (7), 1669–70. The products obtained were found to be identical by NMR to those obtained by the synthesis described above.

EXAMPLE 2

SYNTHESES OF DIHYDROXYPHOSPHORYLETHYL SPECIES

This example illustrates the preparation of certain dihydroxyphosphorylethyl analogs of the compounds prepared in Example 1. Species based on both 1,4,7-triazacyclononane and 1,4,7,10-tetraazacyclododecane are again illustrated in parallel fashion.

A. Synthesis of Per-N-Substituted Dihydroxyphosphorylethyl Phosphonates

Diethyl 2-bromoethylphosphonate, prepared by procedures described in the literature, was reacted separately with the hydrobromide salts of 1,4,7-triazacyclononane and 1,4,7,10-tetraazacyclododecane in water in the presence of excess $K_2CO_3$ at 80° C. for 4–5 hours. The water was then removed by evaporation and chloroform was added to the solids to remove the product from the inorganic salts. The products were purified by chromatography employing neutral alumina and an elution solvent of 10% methanol in chloroform. The perethyl ester groups were removed by hydrolysis using HCl as described in part C of Example 1 above. The pure products were obtained by crystallization from 10% ethanol in water, and their identity was established as N,N',N''-tris(dihydroxyphosphorylethyl)-1,4,7-triazacyclononane and N,N',N'',N'''-tetrakis(dihydroxyphosphorylethyl)-1,4,7, 10-tetraazacyclododecane, respectively, by proton NMR and elemental analysis after accounting for water of hydration.

Those skilled in the art will recognize that this procedure can be employed in an analogous manner to synthesize similar compounds having substituted or unsubstituted alkyl or aryl substitutions on the ethylene carbon atoms by employing correspondingly substituted diethyl 2-bromoethylphosphonate.

B. Synthesis of N,N',N''-tris(dihydroxyphosphorylhydroxyethyl)-1,4,7-triazacyclononane Diethyl epoxyethyl phosphonate, prepared employing known procedures, was combined with a solution of 1,4,7-triazacyclononane in methanol at room temperature, using 3.3 equivalents of the diethyl epoxyethyl phosphonate. The solution was stirred for six hours at 40–50° C. The methanol was evaporated and the residue was dissolved in water. The excess epoxide was then extracted with diethyl ether and the water layer was evaporated. The residue was purified by chromatography using neutral alumina by first eluting the column with chloroform followed by 10% methanol in chloroform. The perethyl ester groups were removed by hydrolysis in HCl as described above. The pure product was obtained by crystallization from 10% ethanol in water. The identity of the product was established as that of N,N',N''-tris(dihydroxyphosphorylhydroxyethyl)-1,4,7-triazacyclononane by proton NMR and elemental analysis after accounting for three molecules of water of hydration.

Those skilled in the art will recognize that the tris-dihydroxyphosphorylaminoethyl analog is similarly prepared by the same procedure, using diethyl ethylenimino phosphonate in place of the diethyl epoxyethyl phosphonate, and that similar compounds bearing substituted or unsubstituted alkyl or aryl substitutions on the ethylene carbon atoms are prepared analogously by employing correspondingly substituted forms of diethyl epoxyethyl phosphonate or diethyl ethylenimino phosphonate. The same procedure can likewise be used to synthesize hydroxyphosphoryl hydroxyethyl and hydroxyphosphoryl aminoethyl derivatives of other polyamines.

EXAMPLE 3

PREPARATION OF METAL CATION COMPLEXES

A. Fe(III) and Cr(III) Complexes of N,N',N''-Tris(dihydroxyphosphorylmethyl)-1,4,7-triazacyclononane In separate syntheses, N,N',N''-tris(dihydroxyphosphorylmethyl)-1,4,7-triazacyclononane in water was combined with an equivalent of a water soluble salt of the appropriate metal cation to be included in the complex (i.e., $FeCl_3.6H_2O$ or $CrCl_3.6H_2O$). The mixtures were heated in a reflux apparatus at 100° C. while base was slowly added in an amount equal to "n" equivalents, where "n" equals the charge of the metal cation. The Fe(III) complex crystallized from the aqueous solution, permitting recovery in high yield. The Cr(III) complex crystallized upon addition of ethanol. The crystallized complex in each case was added to fresh water and sufficient base was added to yield a final pH of >10.0. In the case of the Fe(III) complex, the resulting solution was heated to 100° C. while in the case of the Cr(III) complex, the resulting solution was heated to 140° C. (under pressure). Heating was continued in each case until a single chromatographic species was obtained.

The solutions were then cooled and filtered to remove solids, and acid was added to the flitrate to crystallize or precipitate the complex as before. Additional crystallizations of the complex were performed from water or water/ethanol. The purity of each complex was established by thin layer chromatography (TLC). The identity of each product was established by elemental analysis.

B. Fe(III) Complexes of N,N',N''-Tris(dihydroxyphosphorylethyl)-1,4,7-triazacyclononane and N,N',N''-Tris(dihydroxyphosphorylhydroxyethyl)-1,4,7-triazacyclononane These complexes were prepared following modifications of the procedure of part A above. When solutions of the Fe(III) complex of N,N',N''-tris(dihydroxyphosphorylethyl)-1,4,7-triazacyclononane were acidified, additional products were noted on chromatographic analysis. Consequently, the final recrystallization step requiring acidification was eliminated, and the neutral form of the complex was not isolated as a solid. The tri-sodium salt of the product was purified in an ion exchange column, and the inorganic salts were removed by use of an LH20 column. In the case of the Fe(III) complex of N,N',N''-tris(dihydroxyphosphorylhydroxyethyl)-1,4,7-triazaeyclononane, a single chromatographically distinct product was not obtained using this procedure.

C. Mn(II) and Mn(III) Complexes of N,N',N''-Tris(dihydroxyphosphorylmethyl)-1,4,7-triazacyclononane The procedure for these complexes was modified due to the ease with which redox reactions occurred. The tetra-sodium salt of the Mn(II) complex was formed directly by adding six equivalents of NaOH to a 1:1 mixture of ligand and MnCl$_2$, in water, followed by crystallization of the salt of the complex by addition of ethanol and cooling. To prepare the tri-sodium salt of the Mn(III) complex, a stoichiometric quantity of persulfate ion was added to the tetra-sodium salt of the Mn(II) complex, and the reaction allowed to stand at room temperature until all of the Mn(II) had oxidized to Mn(III). The product was purified by passage through an ion exchange column, and inorganic salts were removed by passage through an LH-20 column. Both products were characterized as single, chromatographically distinct products on TLC.

D. Gd(III) Complexes of N,N',N''-Tris(dihydroxyphosphoryimethyl)-1,4,7-triazacyclononane, N,N',N'',N'''-Tetrakis(dihydroxyphosphorylmethyl)-1,4,7,10-tetraazacyclododecane and N,N',N'',N'''-Tetrakis(dihydroxyphosphorylethyl)-1,4,7,10-tetraazaeyclododecane The tri-sodium salt of the Gd(III) complex of N,N',N''-tris(dihydroxyphosphorylmethyl)-1,4,7-triazacyclononane was made directly from GdCl$_3$.6H$_2$O and the acid form of the ligand by adding equivalent amounts of each to water and heating at 100° C. When the solution was clear, six equivalents of NaOH were added slowly, and the solution was heated for an additional five days. After centrifugation to remove the small amount of residual solids, the solution was dried to give a solid which was characterized as a single, chromatographically distinct product on TLC.

The neutral form of the Gd(III) complex of N,N',N'',N'''-tetrakis(dihydroxyphosphorylmethyl)-1,4,7,10-tetraazaeyclododecane was made from GdCl$_3$.6H$_2$O and the acid form of the ligand by adding equivalent amounts of each to water, followed by slow addition of three equivalents of NaOH. Heating at 90° C. resulted in formation of a gelatinous precipitate. Heating was continued until no further precipitate formed, and the reaction mixture was allowed to cool to room temperature. The precipitate which formed as a result was isolated by centrifugation and washed with water. The washed precipitate was added to water, the pH was raised above 11 by addition of NaOH, and the resulting clear solution was heated overnight at 100° C. The solution was acidified to pH <3.0 with concentrated HCl and was concentrated and cooled, yielding solids which were separated by centrifugation.

The pentameglumine salt of the Gd(III) complex of N,N',N'',N'''-tetrakis(dihydroxyphosphorylethyl)-1,4,7,10-tetraazacyclododecane was made directly from Gd$_2$O$_3$ and the acid form of the ligand by adding 0.5 molecular equivalents of the former and 1.0 molecular equivalents of the latter to water and heating at 90° C. until a clear solution was obtained. After filtration, five equivalents of meglumine were added to the filtrate, and the reaction was heated at 100° C. for 20 hours. After cooling, the reaction mixture was brought to dryness to obtain the solid product.

EXAMPLE 4

PREPARATION OF PHYSIOLOGICAL SALTS

A. Sodium and Meglumine Salts of Fe(III) Complex with N,N',N''-Tris(dihydroxyphosphorylmethyl)-1,4,7-triazaeyclononane The solid form of the Fe(III) complex of N,N',N''-tris(dihydroxyphosphorylmethyl)-1,4,7-triazacyclononane, the complex whose preparation is described in Example 3, part A above, was added to water at room temperature. Sodium hydroxide or meglumine were added to separate solutions of the neutral Fe(III) complex of N,N',N''-tris(dihydroxyphosphorylmethyl)-1,4,7-triazacyclononane until the solutions maintained a pH of 7.0 to 7.4. The solutions were then lyophilized to obtain the solid physiological salts of the complex. These solids, when reconstituted with a suitable aqueous solvent prior to use, are suitable for in vivo administration. In each case, for the sodium salts of the complexes, potentiometric titration demonstrated that the principal form of the complexes at pH 7.0 to 7.4 was the trianion of the complex, and thus that the principal salt forms at this pH were the trisodium and the trimeglumine salt.

B. Meglumine Salt of Cr(III) Complex with N,N',N''-Tris(dihydroxyphosphorylmethyl)-1,4,7-triazacyclononane The solid form of the Cr(III) complex of N,N',N''-tris(dihydroxyphosphorylmethyl)-1,4,7-triazacyclononane, the complex whose preparation is described in Example 3, part A above, was treated with three equivalents of meglumine in a fashion comparable to that described in Example 4, Part A above. Potentiometric titration of the sodium salt of this complex demonstrated that the principal form of the resulting salt at pH 7.0 to 7.4 was the trianion.

Those skilled in the art will recognize that other salts of the subject complexes can be obtained employing similar procedures.

EXAMPLE 5

PRODUCT EVALUATION

In the following studies, the test species are referred to as follows:

TABLE 1

| | Test Species | | |
|---|---|---|---|
| Ref. | Ligand | Paramagnetic Cation | Physiologically Compatible Cation |
| A | N,N',N''-tris(dihydroxyphosphorylmethyl)-1,4,7-triazacyclononane | Fe(III) | trisodium |
| B | N,N',N''-tris(dihydroxyphosphorylmethyl)-1,4,7-triazacyclononane | Fe(III) | tri-meglumine |
| C | N,N',N''-tris(dihydroxyphosphorylethyl)-1,4,7-triazacyclononane | Fe(III) | tri-sodium |
| D | N,N',N''-tris(dihydroxyphosphorylmethyl)-1,4,7-triazacyclononane | Cr(III) | tri-meglumine |
| E | N,N',N''-tris(dihydroxyphosphorylmethyl)-1,4,7-triazacyclononane | Mn(II) | tetra-sodium |
| F | N,N',N''-tris(dihydroxyphosphorylmethyl)-1,4,7-triazacyclononane | Mn(III) | tri-sodium |
| G | N,N',N''-tris(dihydroxyphosphorylmethyl)-1,4,7-triazacyclononane | Gd(III) | tri-sodium |
| H | N,N',N'',N'''-tetrakis(dihydroxy-phosphorylethyl)-1,4,7,10-tetraazacyclododecane | Gd(III) | penta-meglumine |

A. Water Solubility

All of the test species listed above were dissolved in water, demonstrating solubility at concentrations sufficient to be useful as pharmaceutical agents. In particular, test species A and B proved soluble in water at concentrations exceeding 50% (weight/volume).

B. Stability

TLC was performed on test species A and D, both before and after heating at 100° C. for two hours. A single, chromatographically distinct spot which did not vary as a result of the heating was observed in both cases.

C. Toxicity

Physiological salts of the various ligand/metal cation complexes described herein were administered intravenously to mice. The mice were observed for two weeks following such administration, and the results are listed in Table 2 below. In this data, the administered dose is expressed as mM of complex per kg whole body weight (mM/kg), and the administration rate is expressed as mM of complex administered per second or per minute per kg whole body weight (mM/sec/kg or mM/min/kg). The mice were considered to have "survived" administration of each agent if they were alive at the end of the two-week period.

TABLE 2

| | | Toxicity Test Results | | |
|---|---|---|---|---|
| Test | Test Species | Dose | Rate | Survived? |
| (1) | A | 11.8 mM/kg | 0.4 mM/sec/kg | yes |
| (2) | B | 9.8 mM/kg | 0.7 mM/min/kg | yes |
| (3) | C | 10.0 mM/kg | 2.0 mM/min/kg | yes |
| (4) | D | 2.9 mM/kg | 0.5 mM/sec/kg | yes |
| (5) | E | 2.9 mM/kg | 1.1 mM/min/kg | yes |
| (6) | F | 8.0 mM/kg | 2.6 mM/min/kg | yes |
| (7) | G | 3.1 mM/kg | 0.8 mM/min/kg | yes |

When complexes of Fe(III) with N,N',N''-tris(dihydroxyphosphorylmethyl)-1,4,7-triazacyclononane (Test Species A) were prepared employing alternate complexation procedures and which contained multiple forms of the complex as detected by TLC, the toxicity observed was substantially greater than that observed with preparations of this complex prepared employing the procedure described herein and which showed a single, chromatographically distinct product on TLC.

D. In Vivo Distribution And Whole Body Clearance Studies

Radioisotopically labeled analogs of test species selected from those listed above were synthesized, using radioisotopes of Fe(III) (iron-59), Cr(III) (chromium-51) and Gd(III) (gadolinium-153), and employing the general synthesis procedures described above. The resulting complexes were subjected to radiochromatography to insure acceptable radiopurity and identity with the parent complexes. They were then administered intravenously to mice in order to measure in vivo distribution and whole body clearance.

The location of the test species in the mice's bodies and the rate at which the test species were cleared from the mice's bodies after administration were determined by radioassay of tissues and whole body counting, both performed by conventional gamma ray counting techniques. Concentration of activity in tissues was determined as activity per gram of tissue, and whole body counts were expressed as the percentage of whole body activity at a given time with respect to whole body activity, immediately after injection. The results were as follows:

1. Radioisotopes of Test Species A and B.
   In vivo distribution. Within 2 minutes following administration, evidence of concentration of radioactivity in bone and kidneys was seen. By measurements taken one hour after administration, the ratio of the concentration of the test species in bone to that in whole blood was generally over 25:1, while the ratio of their concentration in kidney to that in blood was generally over 10:1. Even after 24 hours, when less than 5% of the administered dose remained in the body (see below), a high ratio of concentration of the test species in bone and kidney to that in blood was maintained. In mice who had a tibia broken two to four weeks prior to the study, the tibia which had suffered the fracture showed significantly greater accumulation of activity than that which was measured in the contralateral normal tibia. All mice showed very low activity in the brain at all times following their administration.

Whole Body Clearance. Within 24 hours of administration, over 95% of both test species had been cleared from the body, almost exclusively through the urine.

2. Radioisotope of Test Species C.

In vivo distribution. One hour after administration, the measured bone-to-blood concentration ratio was greater than 4.5:1, and the measured kidney-to-blood ratio was greater than 5.5:1. A very low concentration of this agent in brain was noted within this first hour.

Whole Body Clearance. Within 24 hours of administration, over 95% of the test species had been cleared from the body.

3. Radioisotope of Test Species D.

In vivo distribution. One hour after administration, the measured bone-to-blood concentration ratio was greater than 6:1, and the measured kidney-to-blood ratio was greater than 10:1. A very low concentration of agent in brain was noted within this first hour.

Whole Body Clearance. Within 24 hours of administration, over 95% of the test species had been cleared from the body, almost exclusively through the urine.

E. Relaxivity Measurements

Measurements of proton longitudinal relaxivity ($1/\tau_1$) were performed on some of the test species listed above, and compared with those obtained using the following complexes outside the scope of this invention: (i) Gd(III) with diethylenetriamine pentaacetic acid (DTPA), and (ii) Fe(III) with N,N'-ethylenebis[(2-hydroxyphenyl)-glycinate] (EHPG). All measurements were obtained using a Bruckner PC/20 Minispec device operating at 20 MHz. All samples were dissolved in 0.1M phosphate buffer at pH 7.2.

The proton longitudinal relaxivity of Test Species A was two to three times greater than that obtained for the Fe(III) complex of EHPG and between 40 and 45% of that obtained for the Gd(III) complex of DTPA. Similar results were obtained for Test Species C.

F. Relative Equilibrium Constant Measurements

The highly colored Fe(III) complex of EHPG (used for comparison in part E of this example) was dissolved in 0.25M phosphate buffer at pH 7.2, and an equimolar quantity of N,N',N''-tris(dihydroxyphosphorylmethyl)-1,4,7-triazacyclononane was added. The solution was heated overnight at 100° C. The resulting solution was devoid of the purple Fe(III) EHPG complex color, and TLC showed only the presence of the Fe(III) N,N',N''-tris(dihydroxyphosphorylmethyl)-1,4,7-triazacyclononane complex.

The reverse experiment was also performed. The Fe(III) complex of N,N',N''-tris(dihydroxyphosphorylmethyl)-1,4,7-triazacyclononane was thus dissolved in 0.25M phosphate buffer at pH 7.2, and an equimolar quantity of EHPG was added. The solution was heated overnight at 100° C. As in the first experiment, the resulting solution was devoid of the purple color of Fe(III) EHPG, and TLC showed only the presence of the Fe(III) N,N',N''-tris(dihydroxyphosphorylmethyl)-1,4,7-triazacyclononane complex.

These results demonstrate the relative stability of the Fe(III) N,N',N''-tris(dihydroxyphosphorylmethyl)-1,4,7-triazacyclononane complex in comparison to the Fe(III) EHPG complex.

The foregoing is offered primarily for purposes of illustration. It will be readily apparent to those skilled in the art that further variations, substitutions and modifications in the substances and procedures involved in the invention beyond those specifically disclosed herein may be made without departing from the spirit and scope of the invention.

What is claimed is:

1. A method of preferentially enhancing magnetic resonance image contrast in bone tissue and other tissue of a patient bearing recognition features in common with bone tissue, said method comprising administering to said patient an effective amount of a pharmaceutical agent comprising a physiologically compatible salt of the complex produced by the addition of a suitable paramagnetic metal cation to a chelator having the formula

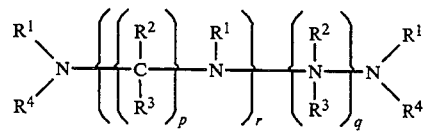

in which:

the $R^1$ moieties are each independently

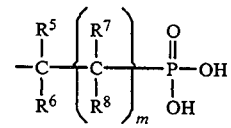

in which $R^5$, $R^8$ and $R^7$ are independently selected from the group consisting of H and alkyl and aryl groups which do not interfere with complexation; $R^8$ is selected from the group consisting of H, OH, $NH_2$, and alkyl and aryl groups which do not interfere with complexation; and m is zero or 1;

the $R^2$ moieties are each independently selected from the group consisting of H and alkyl and aryl groups which do not interfere with complexation;

the $R^3$ moieties are each independently selected from the group consisting of H and alkyl and aryl groups which do not interfere with complexation;

p is 2 or 3;

q is 2 or 3;

r is 2 or 3; and the $R^4$ moieties together form a single divalent group having the formula

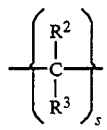

in which $R^2$ and $R^3$ are as defined above, and s is at least 2.

2. A method in according with claim 1 in which r is 2.

3. A method of preferentially enhancing magnetic resonance image contrast in bone tissue and other tissue of a patient bearing recognition features in common with bone tissue, said method comprising administering to said patient an effective amount of a pharmaceutical agent comprising a physiologically compatible salt of the complex produced by the addition of a suitable paramagnetic metal cation to a chelator having the formula

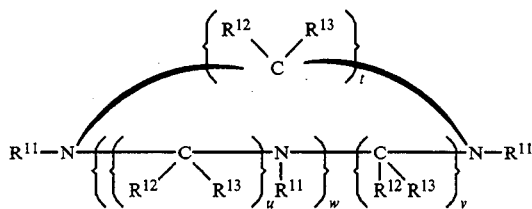

in which:
the $R^{11}$ moieties are each independently

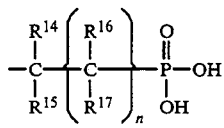

in which $R^{14}$, $R^{15}$ and $R^{16}$ are independently selected from the group consisting of H and alkyl and aryl groups which do not interfere with complexation; $R^{17}$; is selected from the group consisting of H, OH, $NH_2$, and alkyl and aryl groups which do not interfere with complexation; and n is zero or 1;
the $R^{12}$ moieties are each independently selected from the group consisting of H and alkyl and aryl groups which do not interfere with complexation;
the $R^{13}$ moieties are each independently selected from the group consisting of H and alkyl and aryl groups which do not interfere with complexation;
t is 2 or 3;
u is 2 or 3;
v is 2 or 3; and
w is at least 2.

4. A method in accordance with 3 in which $R^{14}$, $R^{15}$ and $R^{16}$ are independently selected from the group consisting of H, $C_1$-$C_8$ alkyl, phenyl and benzyl; and $R^{17}$ is selected from the group consisting of H, OH, $NH_2$, $C_1$-$C_8$ alkyl, phenyl and benzyl.

5. A method in accordance with claim 3 in which $R^{14}$, $R^{15}$ and $R^{16}$ are independently selected from the group consisting of H, $C_1$-$C_4$ alkyl and benzyl; and $R^{17}$ is selected from the group consisting of H, OH, $NH_2$, $C_1$-$C_4$ alkyl and benzyl.

6. A method in accordance with claim 3 in which $R^{14}$, $R^{15}$ and $R^{16}$ are each H; $R^{17}$ is selected from the group consisting of H, OH, $NH_2$, $C_1$-$C_8$ alkyl, phenyl and benzyl; and n is 1.

7. A method in accordance with claim 3 in which $R^{14}$, $R^{15}$ and $R^{16}$ are each H; $R^{17}$ is selected from the group consisting of H, OH, $NH_2$, $C_1$-$C_4$ alkyl and benzyl; and n is 1.

8. A method of accordance with claim 3 in which $R^{14}$, $R^{15}$, $R^{16}$ and $R^{17}$ are each H; and n is 1.

9. A method in accordance with claim 3 in which $R^{14}$ and $R^{15}$ are independently selected from the group consisting of H, $C_1$-$C_8$ alkyl, phenyhl and benzyl; and n is zero.

10. A method in accordance with claim 3 in which $R^{14}$ and $R^{15}$ are independently selected from the group consisting of H, $C_1$-$C_4$ alkyl and benzyl; and n is zero.

11. A method in accordance with claim 3 in which $R^{14}$ and $R^{15}$ are each H; and n is zero.

12. A method in accordance with claim 3 in which the $R^{12}$ and $R^{13}$ moieties are each independently selected from the group consisting of H, $C_1$-$C_8$ alkyl, phenyl and benzyl.

13. A method in accordance with claim 3 in which the $R^{12}$ and $R^{13}$ moieties are each independently selected from the group consisting of H, $C_1$-$C_4$ alkyl and benzyl.

14. A method in accordance with claim 3 in which the $R^{12}$ moieties are each H; and the $R^{13}$ moieties are each independently selected from the group consisting of H, $C_1$-$C_8$ alkyl, phenyl and benzyl.

15. A method in accordance with claim 3 in which the $R^{12}$ moieties are each H; and the $R^{13}$ moieties are each independently selected from the group consisting of H, $C_1$-$C_4$ alkyl and benzyl.

16. A method in accordance with claim 3 in which the $R^{12}$ moieties are each H; and the $R^{13}$ moieties are each independently selected from the group consisting of H and $C_1$-$C_4$ alkyl.

17. A method in accordance with claim 3 in which the $R^{12}$ moieties are each H; and the $R^{13}$ moieties are each independently selected from the group consisting of H and methyl.

18. A method in accordance with claim 3 in which the $R^{12}$ moieties are each H; and the $R^{13}$ moieties are each H.

19. A method in accordance with claim 3 in which t, u and v are each 2.

20. A method in accordance with claim 3 in which w is 2 to 4.

21. A method in accordance with claim 3 in which w is 2 to 3.

22. A method in accordance with claim 3 in which w is 2.

23. A method in accordance with claim 3 in which said paramagnetic metal cation is a cation of an element having an atomic number of 22 to 29 or 58 to 70.

24. A method in accordance with claim 3 in which said paramagnetic metal cation is a cation of an element selected from the group consisting of chromium, manganese, iron and gadolinium.

25. A method in accordance with claim 3 in which said physiological compatible salt is comprised of said complex in combination with at least one cation selected from the group consisting of sodium and N-methylglucamine.

26. A method of preferentially enhancing magnetic resonance image contrast in bone tissue and other tissue of a patient bearing recognition features in common with bone tissue, said method comprising administering to said patient an effective amount of a pharmaceutical agent comprising a physiologically compatible salt of the complex produced by the addition of a suitable paramagnetic metal cation to a chelator having the formula

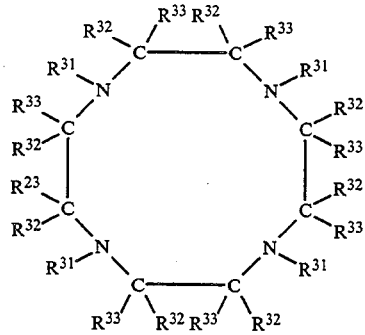

in which:

the $R^{31}$ moieties are each independently

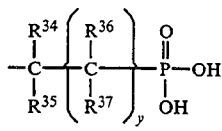

in which $R^{34}$, $R^{35}$ and $R^{36}$ are independently selected from the group consisting of H and alkyl and aryl group which do not interfere with complexation; $R^{37}$ is selected from the group consisting of H, OH, $NH_2$, and alkyl and aryl groups which do not interfere with complexation; and y is zero or 1;

the $R^{32}$ moieties are each independently selected from the group consisting of H and alkyl and aryl groups which do not interfere with complexation; and the $R^{33}$ moieties are each independently selected from the group consisting of H and alkyl and aryl groups which do not interfere with complexation.

27. A method in accordance with claim 26 in which $R^{34}$, $R^{35}$ and $R^{36}$ are independently selected from the group consisting of H, $C_1$-$C_4$ alkyl and benzyl; and $R^{37}$ is selected from the group consisting of H, OH, $NH_2$, $C_1$-$C_4$ alkyl and benzyl.

28. A method in accordance with claim 26 in which $R^{34}$, $R^{35}$ and $R^{36}$ are each H; $R^{37}$ is selected from the group consisting of H, OH, $NH_2$, $C_1$-$C_4$ alkyl and benzyl; and y is 1.

29. A method in accordance with claim 26 in which $R^{34}$, $R^{35}$, $R^{36}$ and $R^{37}$ are each H; and y is 1.

30. A method in accordance with claim 26 in which $R^{34}$ and $R^{35}$ are independently selected from the group consisting of H, $C_1$-$C_4$ alkyl and benzyl; and y is zero.

31. A method in accordance with claim 26 in which $R^{34}$ and $R^{35}$ are each H; and y is zero.

32. A method in accordance with claim 26 in which the $R^{32}$ and $R^{33}$ moieties are each independently selected from the group consisting of H, $C_1$-$C_4$ alkyl and benzyl.

33. A method in accordance with claim 26 in which the $R^{32}$ moieties are each H; and the $R^{33}$ moieties are each independently selected from the group consisting of H, $C_1$-$C_4$ alkyl and benzyl.

34. A method in accordance with claim 26 in which the $R^{32}$ moieties are each H; and the $R^{33}$ moieties are each independently selected from the group consisting of H and $C_1$-$C_4$ alkyl.

35. A method in accordance with claim 26 in which the $R^{32}$ moieties are each H; and the $R^{33}$ moieties are each H.

36. A method in accordance with claim 26 in which $R^{34}$ and $R^{35}$ are each H; y is zero; the $R^{32}$ moieties are each H; and the $R^{33}$ moieties are each H.

37. A method in accordance with claim 26 in which $R^{34}$, $R^{35}$, $R^{36}$ and $R^{37}$ are each H; y is 1; the $R^{32}$ moieties are each H; and the $R^{33}$ moieties are each H.

38. A method in accordance with claim 26 in which $R^{34}$, $R^{35}$ and $R^{36}$ are each H; $R^{37}$ is OH; y is 1; the $R^{32}$ moieties are each H; and the $R^{33}$ moieties are each H.

39. A method in accordance with claim 26 in which $R^{34}$, $R^{35}$ and $R^{36}$ are each H; $R^{37}$ is $NH_2$; y is 1; the $R^{32}$ moieties are each H; and the $R^{33}$ moieties are each H.

40. A method in accordance with claim 26 in which said paramagnetic metal cation is a cation of an element having an atomic number of 22 to 29 or 58 to 70.

41. A method in accordance with claim 26 in which said paramagnetic metal cation is a cation of an element having an atomic number of 24 to 29 or 64 to 68.

42. A method in accordance with claim 26 in which said paramagnetic metal cation is a cation of an element selected from the group consisting of chromium, manganese, iron and gadolinium.

43. A method in accordance with claim 26 in which said physiological compatible salt is comprised of said complex in combination with at least one cation selected from the group consisting of sodium and N-methylglucamine.

44. A method in accordance with claim 26 in which said physiologically compatible salt is the pentameglumine salt of the Gd(III) complex of N,N',N'', N'''-tetrakis(dihydroxyphosphorylethyl)-1,4,7,10-triazacyclononane.

45. A method of preferentially enhancing magnetic resonance image contrast in bone tissue and other tissue of a patient bearing recognition features in common with bone tissue, said method comprising administering to said patient an effective amount of a pharmaceutical agent comprising a physiologically compatible salt of the complex produced by the addition of a suitable paramagnetic metal cation to a cyclic polyazaalkane chelator comprised of a heterocyclic ring containing at least four ring nitrogen atoms having three or more phosphonate groups of the following formula bonded to the ring nitrogen atoms:

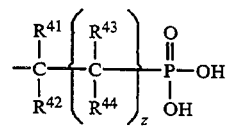

in which:

$R^{41}$, $R^{42}$ and $R^{43}$ are independently selected from the group consisting of H and alkyl and aryl groups which do not interfere with complexation;

$R^{44}$ is selected from the group consisting of H, OH, $NH_2$, and alkyl and aryl groups which do not interfere with complexation; and z is zero or 1.

46. A method of preferentially enhancing magnetic resonance image contrast in bone tissue and other tissue of a patient bearing recognition features in common with bone tissue, said method comprising administering to said patient an effective amount of a pharmaceutical agent comprising a physiologically compatible salt of the complex produced by the addition of a suitable paramagnetic metal cation to a cyclic polaza chelator comprised of a heterocyclic ring containing at least four ring nitrogen atoms with phosphonate groups replacing the hydrogen groups of ring nitrogen atoms.

* * * * *

UNITED STATES PATENT AND TRADEMARK OFFICE
CERTIFICATE OF CORRECTION

PATENT NO. : 5,380,515

DATED : January 10, 1995

INVENTOR(S) : Harry S. Winchell, et al.

It is certified that error appears in the above-identified patent and that said Letters Patent is hereby corrected as shown below:

At column 2, line 8, change "beating" to --bearing--;

At column 3, line 65, formula in Example 1, change 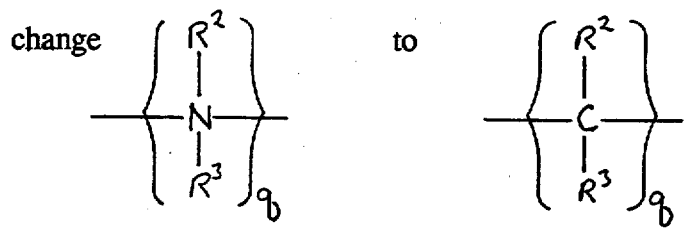

At column 5, line 65, change "holmlure" to --holmium--;
At column 9, line 8, change "1,4,7-triazaeyelonononane" to --1,4,7-triazacyclononane--;
At column 11, line 44, change "1,4,7-triazaeyclononane" to --1,4,7-triazacyclononane--;

At column 15, line 35, formula in claim 1 change 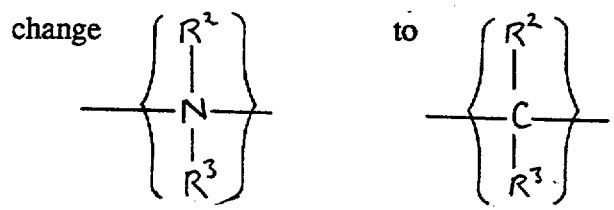

UNITED STATES PATENT AND TRADEMARK OFFICE
CERTIFICATE OF CORRECTION

PATENT NO. : 5,380,515
DATED : January 10, 1995
INVENTOR(S) : Harry S. Winchell, et al.

It is certified that error appears in the above-indentified patent and that said Letters Patent is hereby corrected as shown below:

At column 16, line 50, change "$R^5$, $R^8$ and $R^7$" to --$R^5$, $R^6$, and $R^7$--.

Signed and Sealed this

Fifteenth Day of August, 1995

Attest:

BRUCE LEHMAN

Attesting Officer     Commissioner of Patents and Trademarks